United States Patent [19]
Weiner et al.

[11] Patent Number: 5,593,698
[45] Date of Patent: Jan. 14, 1997

[54] SUPPRESSION OF PROLIFERATIVE RESPONSE AND INDUCTION OF TOLERANCE WITH POLYMORPHIC CLASS II MHC ALLOPEPTIDES

[75] Inventors: Howard L. Weiner, Brookline; David A. Hafler, West Newton; Charles B. Carpenter, Weston; Mohamed Sayegh, West Roxbury; Zhengyi Zhang, Needham, all of Mass.

[73] Assignee: Autoimmune, Inc., Lexington, Mass.

[21] Appl. No.: 27,127

[22] Filed: Mar. 5, 1993

Related U.S. Application Data

[63] Continuation-in-part of Ser. No. 607,826, Oct. 31, 1990, abandoned, and a continuation-in-part of Ser. No. 871,289, Apr. 20, 1992, abandoned, and a continuation-in-part of Ser. No. 961,779, Oct. 15, 1992, abandoned, which is a continuation-in-part of Ser. No. 977,737, Nov. 13, 1992, abandoned.

[51] Int. Cl.⁶ .................... A61K 35/14; A01N 63/00; C07K 1/00; C07K 14/00
[52] U.S. Cl. .................... 424/534; 424/93.71; 530/350
[58] Field of Search .................... 424/93.71, 534; 530/350

[56] References Cited

PUBLICATIONS

Benichou, et al, 1990, "Immunogenuity and tolero–genicity of . . . " J. Exp. Med. 172:1341–1346.
Sayegh, et al, 1992, "Induction of immunity and oral tolerance with . . . " PNAS 89:7762–7766.
Nuchtern et al., *Nature*, 343:74–76, 1990.
Parham et al., *Nature*, 325:625–628, 1987.
Chen et al., *J. Exp. Med.*, 172:779–788, 1991.
Mowat, *Immunology Today*, 8:93–98, 1987.
Sayegh et al., *Transplantation*, 53(1):163–166, 1992.
Chao et al., *Immunogenetics*, 29:231–234, 1989.
Whitacre et al., *J. Immunol.*, 147:2155–2163, 1991.
Nagler–Anderson et al., *Proc. Natl. Acad. Sci. USA*, 83:7443–7446, 1986.
Lider et al., *J. Immunol.*, 142:748–752, 1989.
Miller et al., *Proc. Natl. Acad. Sci. USA*, 89:421–425, 1992.
Falk et al., *Nature*, 351:290–296, 1991.
Rudensky et al., *Nature*, 353:622–627, 1991.
Higgins, *J. Immunol.*, 140:440–445, 1988.
Guillet, J. G. *Science* 235:865–70, Feb. 1987.
Zamvil, S. S. et al., *Nature* 324:258–60, Nov. 1986.
Wood, K. J. et al., *Transplanation* 39:56–62, No. 1, 1985.
Liu, Z. et al., *J. Exp. Med.* 175:1663–68, Jun. 1992.
Guillet, J. G. *Nature* 324:260–262, Nov. 1986.

*Primary Examiner*—Lynette F. Smith
*Attorney, Agent, or Firm*—Darby & Darby, P.C.

[57] ABSTRACT

Described are methods for: (a) suppressing the ability of T-cells from a mammal to proliferate in response to stimulation by nonself mammalian tissue; and (b) suppressing immune response which leads to allograft rejection in a mammal receiving an allograft from a donor mammal. The methods involve orally administering to the mammal to be thus treated a composition comprising at least one of: (i) a major histocompatibility complex Class II antigen from a second nonself mammal or from tissue of a mammal syngeneic to said nonself mammal; (ii) at least one synthetic peptide corresponding to a T-cell suppressive fragment of said Class II antigen, said composition being administered in an amount effective to suppress said proliferation. The foregoing compositions are also described.

3 Claims, 8 Drawing Sheets

FIG. 1

```
            10         20         30         40         50
RT1.Bβu    QRLRRDFLVQFKPYCYFTNGTQRIRNVIRYIYNREEYLRYDSDVGEYRAV

RT1.Bβ1    ........................---------Q---------------Q 60         70         80         90
           TELGRPSAEYFNKQ*Y*LERTRAELDTVCRHNYEKTEVPTSL

---------------*-*--Q--------------------..

10         20         30         40         50
RT1.Dβu    RDPTPRFLGYLKPECHFYNGTNRVRLLARLIYNREEYARFDSDVGEYRAV

RT1.Dβ1    ........................------Y--------T--------F---

60         70         80         90
           TELGRPSAEYRNKQKEPMERRRATVDTYCRHNYEIFDRFL

```
                  10        20        30        40        50
RT1.Bβu    QRLRRDFLVQFKPYCYFTNGTQRIRNVIRYIYNREEYLRYDSDVGEYRAV

RT1.Bβ1    ............................---------Q---------------Q 60        70        80        90
           TELGRPSAEYFNKQ*Y*LERTRAELDTVCRHNYEKTEVPTSL

---------------*-*--Q---------------------..

10        20        30        40        50
RT1.Dβu    RDPTPRFLGYLKPECHFYNGTNRVRLLARLIYNREEYARFDSDVGEYRAV

RT1.Dβ1    ............................------Y--------T--------F---

60        70        80        90
           TELGRPSAEYRNKQKEPMERRRATVDTYCRHNYEIFDRFL

----------Y-----Y--QI------A-K-D-.......
```

SUPPRESSION OF PROLIFERATIVE RESPONSE AND INDUCTION OF TOLERANCE WITH POLYMORPHIC CLASS II MHC ALLOPEPTIDES

This application is a continuation-in-part of U.S. patent application Ser. No. 07/607,826 filed Oct. 31, 1990, abandoned, U.S. patent application Ser. No. 07/871,289 filed Apr. 20, 1992, abandoned, a continuation-in-part of Ser. No. 07/607,826, abandoned and U.S. patent application Ser. No. 07/961,779 filed Oct. 15, 1992, abandoned, which is a continuation-in-part of Ser. No. 07/977,737, Nov. 13, 1992, now abandoned, all incorporated by reference.

FIELD OF THE INVENTION

The present invention is directed to formulations and methods for suppressing lymphocyte proliferation and controlling the immune response of mammals against the introduction of foreign tissue. The invention also includes methods for prolonging the survival of transplanted organs and tissues.

Recent work with synthetic peptides representing portions of the polymorphic regions of mouse and human Class I and II major histocompatibility complex (MHC) molecules indicates that they can be bound to MHC molecules and elicit a T cell response in vitro (Benichou, G., et al. (1990) *J. Exp. Med.* 172: 1341–1346; Nuchtern, J. G., et al. (1990) *Nature* 343: 74–76; Olson, C. A., et al. (1989) *Proc. Natl. Acad. Sci. USA* 86: 1031–1035; Parham, P., et al. (1987) *Nature* 325: 625–628; and Chen, B. P., et al. (1991), *J. Exp. Med.* 172: 779–788). There is no information on the induction of immunity or tolerance by administration of synthetic MHC peptides in vivo. The oral route of administration of antigens has been shown to induce immune hyporesponsiveness (Mowat, A. (1987) *Immunology Today* 8: 93–98). In the parent application, we have disclosed that oral administration of allogeneic splenocytes to inbred rats down-regulates the systemic cell mediated immune response in vitro and in vivo.

BRIEF DESCRIPTION OF THE FIGURES

FIG. 1: Amino acid sequences of the synthetic MHC RT1.B$^u$ and RT1.D$^u$ peptides aligned with those of RT1$^l$. Dots denote unknown sequences while dashes denote identical sequences. Stars denote absent sequences.

FIG. 6: Amino acid sequences of the synthetic MHC RT1.Bβ$^u$, RT1.Bβ$^1$, RT1.Dβ$^u$ and RT1.Dβ$^1$ peptides. Dots denote unknown sequences while dashes denote identical sequences. Stars denote absent sequences.

SUMMARY OF THE INVENTION

Figure 2A:
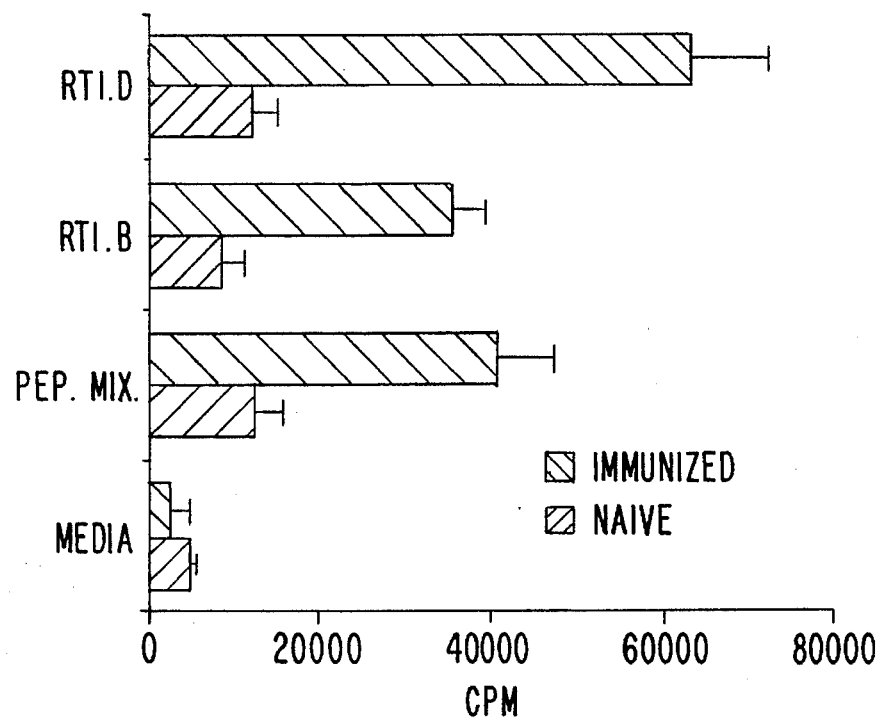
FIG. 2:
A. Direct proliferation of lymphocytes harvested from naive and immunized (with the entire allopeptide mixture) animals and incubated with the entire peptide mixture (PEP.MIX), RT1.B, or RT1.D allopeptides. Bars represent mean cpm ±SEM of a representative experiment performed in quadruplicates (5 experiments).
B. Proliferation of nylon wool non-adherent mononuclear cells harvested from immunized (with the entire allopeptide mixture) animals to the entire peptide mixture (PEP.MIX), RT1.B, or RT1.D allopeptides presented by syngeneic nylon wool adherent cells. Bars represent mean cpm ±SEM of a representative experiment performed in quadruplicates (4 experiments).

The immunogenicity and tolerogenicity of Class II major histocompatibility complex (MHC) allopeptides were tested in the rat in vivo. Inbred LEW (RT1$^l$) rats, used as responders, were immunized in the foot pad with a mixture of 8 Class II synthetic MHC allopeptides emulsified in complete Freund's adjuvant. The sequences of these peptides represented the full length second domain of RT1.B$^u$ and RT1.D$^u$ (WF) β chains. In vitro, responder lymphocytes harvested from popliteal and inguinal lymph nodes of immunized animals exhibited significant proliferation to the MHC allopeptide mixture. In addition, these responder lymphocytes significantly proliferated to allogeneic WF (RT1$^u$) stimulator cells, when compared to naive controls in the standard one-way mixed lymphocyte response (MLR) (relative response: 2.65±0.2, n=6). In vivo, peptide-immunized LEW animals were challenged in the ear 2 weeks after immunization with either the allopeptide mixture or freshly prepared and irradiated allogeneic WF splenocytes. When compared to naive controls, these animals had significant delayed type hypersensitivity (DTH) responses both to the allopeptide mixture and to allogeneic (WF) splenocytes, but not to syngeneic LEW or third party allogeneic (BN) splenocytes.

Oral administration of the allopeptide mixture to LEW responder rats daily for 5 days before immunization resulted in a significant reduction of DTH responses both to the allopeptide mixture (77% reduction, p=0.002) and to allogeneic (WF) splenocytes (70% reduction, p=0.008). This reduction was antigen specific, since there was no reduction of DTH responses to mycobacterium tuberculosis.

These data demonstrate that lymphocytes from animals immunized with polymorphic Class II MHC allopeptides can recognize and proliferate to the same amino acid sequences present on allogeneic cell surface MHC molecules. In addition, oral administration of these peptides down-regulates the systemic cell-mediated immune response in a specific fashion. The present invention is directed to use of synthetic MHC allopeptides to provide specific suppression of proliferative lymphocyte response to Class II MHC antigens of allogeneic tissue and to induce specific immune tolerance to allografts.

DETAILED DESCRIPTION OF THE INVENTION

All cited documents are incorporated by reference in their entirety.

The availability of sequence data for the variable domains of MHC molecules has made it possible to synthesize peptides representing various portions of the native cell surface molecules and to use these peptides to assess immunogenicity and tolerogenicity. The data show that rat polymorphic Class II β MHC allopeptides of 2 loci, RT1.B β and RT1.D β, are immunogenic in vivo as assessed by lymphocyte proliferation in vitro and by DTH responses in vivo. Moreover, when administered orally, these MHC allopeptides are tolerogenic; they induce a state of immune hyporesponsiveness which is antigen-specific.

The data also show that, in addition to polymorphism, the native location of the allopeptide, β-pleat vs. α-helix, appears to be an important determinant of immunogenicity and tolerogenicity. These experiments test the ability of responder (LEW) antigen-presenting cells to bind the β-pleat allopeptide fragments. The α-helix allopeptides serve as negative controls. Although autologous sequences could also be used for these studies, the work of Benichou et al., *J. Exp. Med.* 172:1341–1346 (1990) in the mouse suggests that self-tolerance may not develop to autologous β-pleat sequences. These authors screened five autologous class II mouse MHC peptides and showed that two β-pleat fragments can bind to self MHC molecules and are immunogenic, and that neonatal tolerance could be induced after intraperitoneal injection of an immunogenic peptide. Similar in vitro immunogenicity data in humans have been presented by Liu and Suciu-Foca, *Hum. Immunol.* 32 (Suppl.), 4 (1991) using allopeptide fragments derived from the first domain of HLA-DRB1*0101. Only a β-pleat fragment was immunogenic in the example studied by these co-authors.

Recent work with mouse and human peptides, representing portions of the polymorphic regions of Class I and II MHC molecules, indicates that exogenous allopeptides and self peptides are taken up by antigen presenting cells in vitro and presented on MHC molecules, presumably by the endogenous process of pinocytosis, processing in the Golgi, and transport to the cell surface bound to an MHC molecule for recognition. Demonstration by Chen et al., supra, that a Class I synthetic peptide can be presented on an intact Class II molecule via the exogenous pathway shows that some T cell clones recognize alloantigen which has been processed and presented as peptides in a self-MHC binding site. Self-MHC or allo-MHC peptides may therefore be processed in a manner identical to any other peptide moiety, although recognition of intact MHC molecules which bind endogenous peptides may be a major route of acquisition of immunity to cells or grafts (Eckels, D. D. (1990) *Tissue Antigens* 35: 49–55). The present data demonstrate that animals immunized with Class II MHC allopeptides will recognize and respond to allogeneic cells in vitro and in vivo, indicating that a significant number of T cell clones will recognize polymorphic amino acid sequences on intact cell surface MHC molecules. (Alternatively, the targets could be peptides presented by allo- or self-MHC.)

The route of administration of MHC allopeptides and the qualitative and quantitative aspects of peptide processing and presentation could be determinants of the induction of immunity or tolerance to alloantigens.

Introduction of autoantigens into the intestinal tract will suppress the immune response in several experimental autoimmune models (Mowat, et al., supra). The most extensively studied is the experimental autoimmune encephalomyelitis (EAE) (Higgins, P. J., et al. (1988) *J. Immunol* 140: 440–445; Khoury, S. J., et al. (1990) *Cell Immunol.* 131: 302–310; and Whitacre, C. C., et al. (1986) *J. Immunol.* 144: 2115–2163. Other experimental models where oral administration of antigen results in immunologic unresponsiveness or "oral tolerance" include experimental autoimmune uveoretinitis (Nussenblatt, et al., *J. Immunol.* 144:1689–1695, 1989), collagen-induced and adjuvant-arthritis (Nagler-Anderson, C., et al. (1986) *Proc. Natl. Acad. Sci. USA* 83: 7443–7446; and Zhang, Z. J., et al. (1990) *J. Immunol.* 145: 2489–2493), and diabetes in NOD mice (Zhang, Z. J., et al. (1991) *Proc. Natl. Acad. Sci. USA* 88: 10252–10256). The mechanisms mediating the tolerizing effects of oral administration of antigen have been studied in the EAE model where it is possible to adoptively transfer protection against EAE with CD+8 cells from mesenteric lymph nodes and spleens of animals orally tolerized with myelin basic protein (Lider, O., et al. (1989) *J. Immunol.* 142: 748–752). More recently, Miller et al. showed that these suppressor T cells suppress in vitro and in vivo immune responses by the release of TGF-β1. Others have reported that clonal anergy may also play a role in oral tolerance for MBP in EAE (Whitacre, et al., *J. Immunol*, 147:2155–2163). There is initial evidence in EAE that synthetic peptides can induce tolerance after oral administration (Higgins, et al., *J. Immunol.* 140:440–445). In the mouse, intravenous $CI_{12-26}$ peptide (amino acids 12–26 of lambda repressor protein) produces long term tolerance which does not function by a suppressor mechanism, and is presumably mediated by T cell anergy. In the alloimmune system, we have shown that oral administration of allogeneic splenocytes to inbred rats down-regulates the cell mediated immune response to histocompatibility antigens and prevents sensitization by transplants or allografts (data not shown). We have also demonstrated that oral administration of allogeneic splenocytes is associated with selective inhibition of responder (Type 1 T-helper) Th1-like cell function, and that this inhibition may be mediated by inhibitory cytokines secreted by CD4+ Th2-like cells (Hancock, W. W., et al., *J. Am. Soc. Neph.* 2:782 (1991)). The present experiments demonstrate that oral administration of Class II MHC allopeptides to inbred rats induces a state of specific immunologic hyporesponsiveness; either RT1.D or RT1.B β chain peptides produce comparable reduction of DTH response to whole spleen cells which bear both sets of incompatibilities, as well as α chain and RT1.H Class II, and RT1.A Class I, differences. Therefore, induction of negative regulatory pathways must play a major role in this form of tolerance. This can be used to advantage to induce tolerance to grafts or transplanted organs.

There are data to indicate that peptides presented on Class I MHC molecules are monomers (Falk, K., et al. (1991) *Nature* 351: 290–296), while those presented by Class II MHC molecules are 13–17 amino acids in length (Rudensky, A. Y., et al. (1991) *Nature* 353: 622–627). There are no such data available for MHC allopeptides.

The mechanisms by which oral and intravenous administration of allogeneic splenocytes prevents sensitization by skin allografts were also studied. LEW rats were sensitized with BN skin allografts 7 days prior to receiving heterotopic (LEW×BN) F1 vascularized cardiac allografts. While unsensitized cardiac allografts were rejected on day 6–8, control sensitized grafts were rejected within 24–48 hours. Oral administration of BN splenocytes during the sensitization phase (between skin and heart grafting) prevented this accelerated allograft rejection and prolonged cardiac allograft survival to 7 days. Intravenous administration of BN splenocytes ($50 \times 10^6$ daily for 5 days starting on day of skin grafting) also prevented accelerated cardiac allograft rejection and prolonged graft survival to $9 \pm 1$ days (n=5). Immunoperoxidase studies of cardiac allografts harvested 24–48 hours post-transplant showed that when compared to sensitized controls, animals which received oral splenocytes had reduced deposition of IgG (1/1000 vs 1/4000,), IgM (1/1000 vs 1/6000), C3 (1/4000 vs 1/16000) and fibrin (1/4000 vs 1/16000) titers in the graft. There was also decreased cellular infiltration with macrophages ($18 \pm 8$ vs $37 \pm 8$ cells/HPF, $p<0.01$), T cells ($5 \pm 3$ vs $19 \pm 7$, $p<0.01$), and IL-2R+ T cells ($5 \pm 3$ vs $15 \pm 4$, $p<0.01$). In addition, there was significant reduction of infiltrating mononuclear cells stained with antibodies to IL-1, IL-2, IL-6, IL-8, IFN-γ, and TNF. In contrast, these grafts showed markedly increased IL-4 staining (most mononuclear and all endothelial cells), as compared to control grafts (20% of mononuclear cells and only focal endothelium). Comparative immunoperoxidase studies of cardiac allografts harvested from animals which received the intravenous splenocytes showed similar changes of reduced humoral deposits and cellular infiltrates as seen in the oral splenocytes group, but cytokine staining was different; there was increased staining for both IL-1 on endothelium and IFN-γ on NK cells, while IL-4 staining was not increased relative to control grafts.

Therefore, both oral and intravenous administration of alloantigen down-regulate the immune system but by different mechanisms. Oral administration of alloantigen effects selective inhibition of Th1-like cell function (IL-2 and IFN-γ production), and activation of Th-2 like cells which secrete inhibitory cytokines (IL-4 and possibly IL-10). The mode of action of intravenous alloantigen administration may involve a transient state of T cell anergy.

EXPERIMENTAL

1. Animals: LEW, WF, and BN rats, 8–10 weeks old, were obtained from Harlan Sprague Dawley Inc. (Indianapolis, Ind.) or were bred inhouse.

2. Allopeptides: The RT1.B β and RT1.D β domains of RT1$^u$ (WF) were selected, and 4 overlapping peptides of 24–25 amino acids (1–25 (SEQ.ID. No. 1), 20–44 (SEQ.ID. No. 2), 39–64 (SEQ.ID. No. 3), 68–92 (SEQ.ID. No. 4) for RT1.B, and 1–25 (SEQ.ID. No.5), 20–44 (SEQ.ID. No. 6), 39–64 (SEQ.ID. No. 7), 60–84 (SEQ.ID. No. 8) for RT1.D) were synthesized by solid phase synthesis for each locus (i.e. a total of 8 peptides), using published sequences of the Class II β chain (Chao, N. J., et al. (1989) *Immunogenetics* 29: 231–234). FIG. 1 shows these polymorphic sequences aligned with those of the β chains of RT1[1] (LEW). Peptides which were used for in vitro proliferation assays were purified by high pressure liquid chromatography yielding>95% purity as determined by amino acid analysis.

3. Proliferation Assay: Responder LEW rats were immunized subcutaneously in the foot pad with 100 µg of the mixture of the four RT1.B$^u$ and four RT1.D$^u$ peptides (12.5 µg each) in complete Freund's adjuvant. Popliteal and inguinal lymph nodes were harvested 1 week after immunization and mashed through 60-gauge sterile stainless steel sieves. The recovered cells were then washed twice and resuspended into RPMI 1640 medium (Microbiological Associates Inc.), containing 10% fetal calf serum, 100 U/ml penicillin and 100 µg/ml streptomycin, $2 \times 10^{-5}$M 2-mercaptoethanol, and 5 mM HEPES. T and B cells were separated by nylon adherence as described (Frankel, A. H., et al. (1989) *Transplantation* 48: 639–646). Responder unseparated LEW lymphocytes ($3 \times 10^5$) were cultured in 96-well flat bottom plates (Costar) with 10–50 µg of the mixture of RT1.B$^u$, RT1.D$^u$, or both, sets of allopeptides for 30 minutes at 37° C. The cells were then washed twice to remove excess peptides before adding the nylon wool nonadherent responder T cells ($2 \times 10^5$). Negative control wells were set up with culture medium only. LEW×WF one way MLRs were set up by using equal numbers of responder LEW and allogeneic WF stimulator lymphocytes (prepared as described for LEW lymphocytes and irradiated with 3000 Rads) per well. The plates were incubated at 37° C. with 5% $CO_2$ for four days before they were pulsed for 6 hours with $^3$H-thymidine (1 µCi/well, NEN Dupont) and harvested with a PHD cell harvester (Cambridge Technology). Proliferation was assayed by $^3$H-thymidine incorporation measured by a Beckman liquid scintillation counter. Experiments were set up in quadruplicates, and results expressed as mean counts per minute (±SEM), or relative response=(Experimental-Background cpm). (Control-Background cpm)

4. Delayed Type Hypersensitivity (DTH) Response: LEW rats, used as responders, were immunized subcutaneously in the foot pad with 100 µg of the mixture of four RT1.B$^u$ (50 µg) and four RT1.D$^u$ (50 µg) peptides in complete Freund's adjuvant (12.5 µg of each peptide). These animals were challenged subcutaneously 2 weeks later in one ear with 10 µg of the peptide mixture and in the other ear with freshly prepared and irradiated (3000 Rads) splenocytes ($10 \times 10^6$) from WF (RT1$^u$), syngeneic LEW (RT1[1]), or third party BN (RT1$^n$). The DTH responses were measured with micrometer caliper (Mitutoyo, Japan) by a blinded observer as the delta ear thickness before and 2 days after the challenge (inches $\times 10^{-2}$). Experiments were performed using 5 animals in each study group. P values were calculated using the student t-test.

EXAMPLE 1

Assessment of the Immunogenicity of Class II MHC Allopeptides In Vitro

Figure 2B:
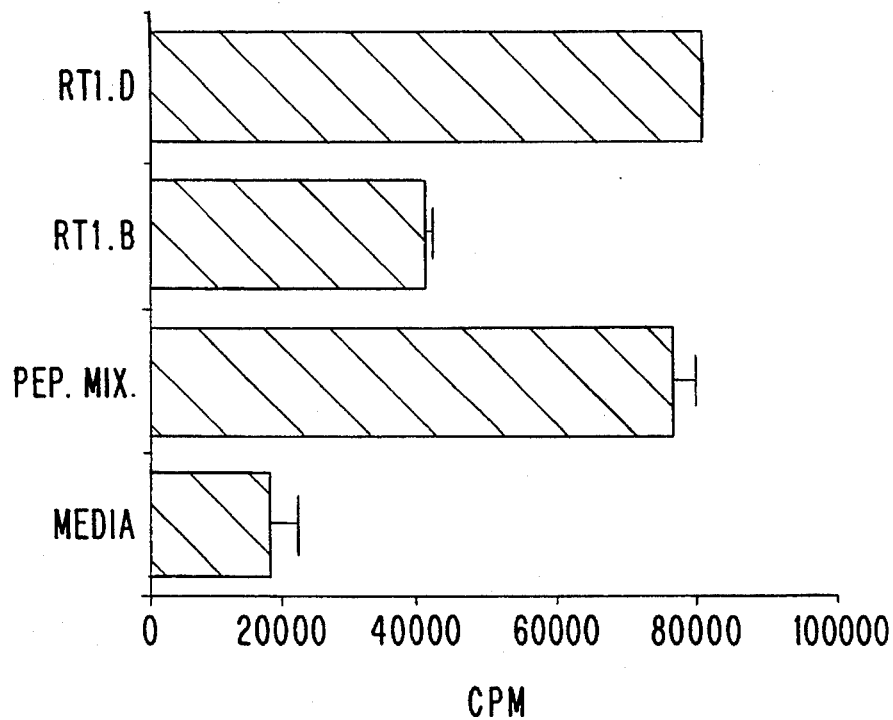

In order to test the immunogenicity of the synthetic RT1.B and RT1.D allopeptides, lymphocytes harvested from responder LEW animals immunized with the mixture of 8 allopeptides 1 week earlier were compared to naive controls for their ability to proliferate to the allopeptides in a standard 96 hour proliferation assay. As shown in FIG. 2A, while naive lymphocytes had only minimal proliferation, immunized animals exhibited significant proliferation to the allopeptide mixture, as well as to individual allopeptides of RT1.B (4 peptides) and RT1.D (4 peptides). In addition, when compared to naive controls, responder lymphocytes from immunized animals exhibited significantly increased proliferation to allogeneic WF stimulator cells in the standard one way MLR (relative response=2.65±0.2, n=6, data not shown). In order to formally test whether syngeneic antigen presenting cells can bind and present MHC allopeptides, nylon wool adherent LEW lymph node cells were preincubated with the entire allopeptide mixture, or with the RT1.B or RT1.D allopeptides separately. After washing, responder T cells were added to the cultures. FIG. 2B shows that T cells from immunized animals proliferate to syngeneic antigen presenting cells which had been preincubated with the MHC allopeptides.

These data demonstrate that the synthetic Class II MHC allopeptides are immunogenic in vivo, as assessed by lymphocyte proliferation in vitro. Furthermore, lymphocytes from animals immunized with these allopeptides proliferate more vigorously to allogeneic cell surface MHC molecules.

EXAMPLE 2

Immunogenicity of Class II MHC Allopeptides by DTH In Vivo

Figure 3A:
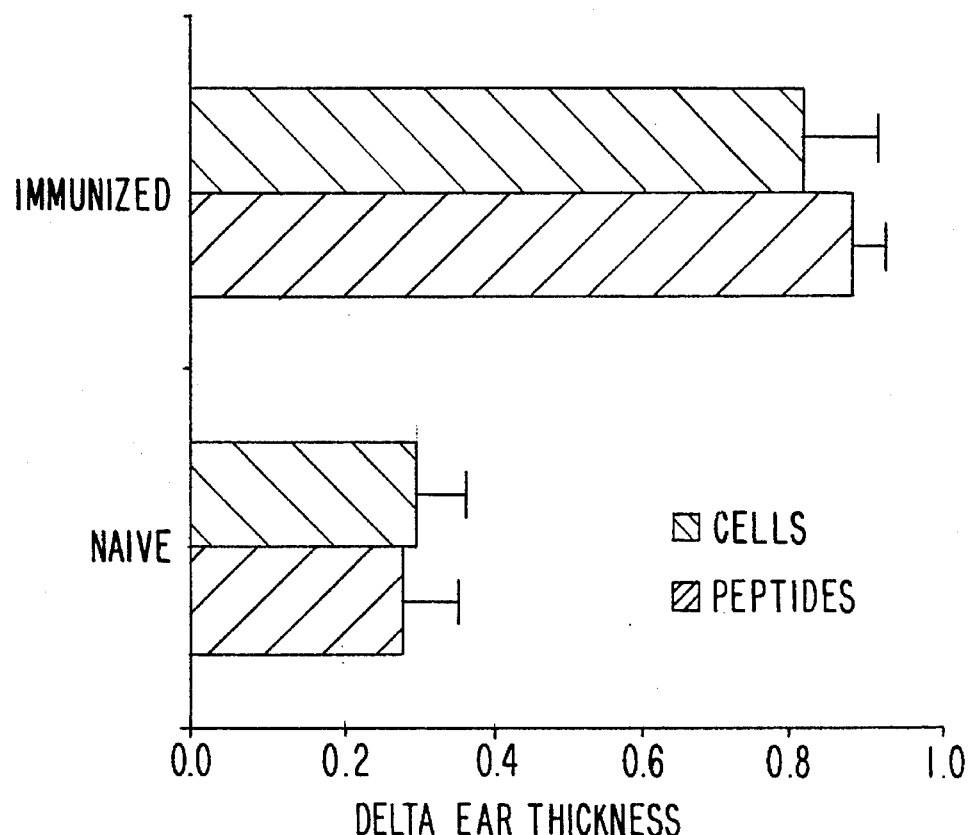
FIG. 3:
A. DTH responses of naive and immunized (with the entire allopeptide mixture, 5 experiments) animals challenged with the peptide mixture (Peptides) or WF splenocytes (Cells). Bars represent mean delta ear thickness in inches×10$^{-2}$ (±SEM) of a representative experiment (n=5 in each group).
B. DTH responses of RT1.B immunized (4 experiments) or RT1.D immunized (5 experiments) animals challenged with the respective allopeptides (Peptides) or WF splenocytes (Cells). Bars represent mean delta ear thickness in inches×10$^{-2}$ (±SEM) of a representative experiment (n=5 animals in each group).
Figure 3B:
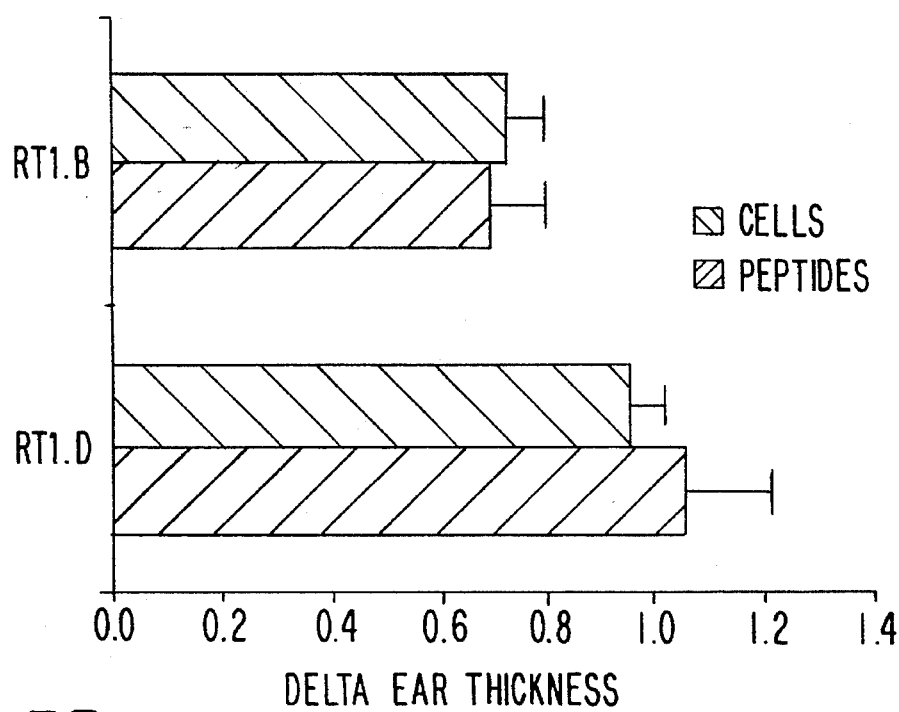

LEW animals which were immunized with the entire allopeptide mixture had significant DTH responses both to the allopeptides and to freshly prepared allogeneic WF splenocytes (FIG. 3A). These responses were antigen specific, since the immunized animals had minimal DTH responses to syngeneic LEW (delta ear thickness in inches × $10^{-2}$=0.22±0.07 vs 0.67±0.06, p<0.001, n=5 in each group) or allogeneic third party BN splenocytes (delta ear thickness=0.12±0.06 vs 0.67±0.06, p<0.001, n=5 in each group). In addition, immunization with RT1.B or RT1.D allopeptides separately resulted in significant DTH responses both to the respective allopeptide mixture and to allogeneic WF splenocytes (FIG. 3B). These data further demonstrate that the synthetic Class II MHC allopeptides are immunogenic in vivo, and that lymphocytes from animals immunized with these allopeptides can respond to polymorphic amino acid sequences on, or derived from, allogeneic cell surface MHC molecules.

EXAMPLE 3

Tolerogenicity of Orally Administered Class II MHC Allopeptides

Figure 4A:
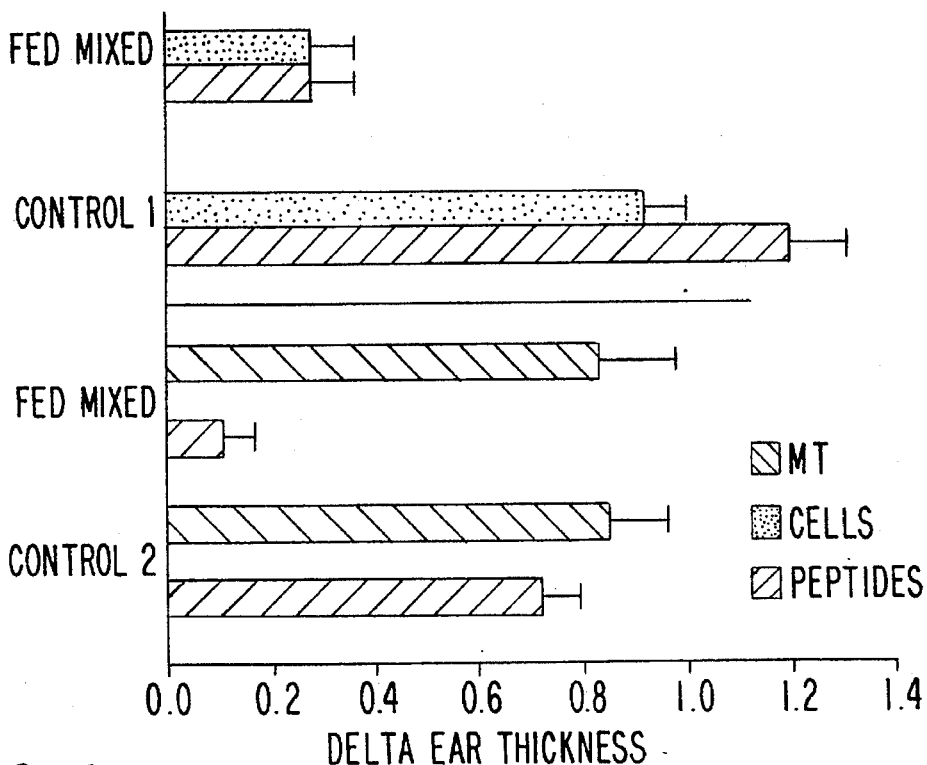
FIG. 4:
A. Reduction of DTH responses by oral administration of the entire allopeptide mixture. Experiment 1, lower panel: animals were immunized with the entire allopeptide mixture and challenged with the peptide mixture (Peptides) or WF splenocytes (Cells). Experiment 2, upper panel: animals were immunized with the entire allopeptide mixture and challenged with the peptide mixture (Peptides) or mycobacterium tuberculosis (MT). Bars represent mean delta ear thickness in inches×10$^{-2}$ (±SEM) (n=5 animals in each group) of control (CONTROL 1 and 2) and peptide fed (FED MIXED) animals.
B. Reduction of DTH responses by oral administration of RT1.B or RT1.D allopeptides. Animals were immunized with RT1.B or RT1.D and challenged with the respective allopeptides (Peptides) or mycobacterium tuberculosis (Cells). Bars represent mean delta ear thickness in inches×10$^{-2}$ (±SEM) (n=5 animals in each group) of control (CONT RT1.B, CONT RT1.D) and peptide fed (FED RT1.B, Fed RT1.D) animals (2 experiments).
Figure 4B:
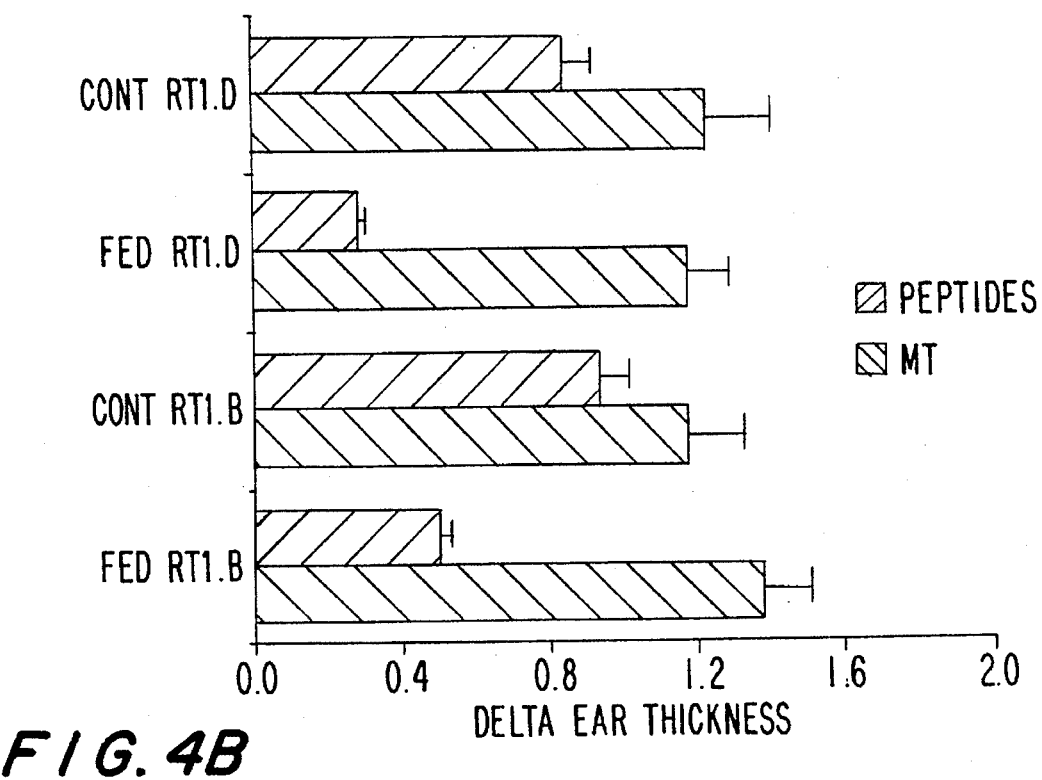

The ability of synthetic Class II MHC allopeptides to induce immune hyporesponsiveness after oral administration was assessed as follows: LEW responder animals were fed 100 μg of the entire allopeptide mixture (8 peptides, 12.5 μg each), or 50 μg of RT1.B or RT1.D, by gavage daily for 5 days. Three days after the last feeding the animals were immunized with the allopeptide mixture and DTH responses determined 2 weeks later. FIG. 4A (lower panel) shows that animals fed all 8 peptides had significantly marked reduction of DTH responses to the same allopeptide mixture (77% reduction, p=0.001) as well as to WF splenocytes (70% reduction, p=0.003), when compared to unfed controls. This reduction was antigen specific since there was no reduction of DTH responses to mycobacterium tuberculosis (the antigen present in complete Freund's adjuvant) (FIG. 4A, upper panel). When either RT1.B or RT1.D allopeptides were fed separately (FIG. 4B), significant reduction of antigen specific DTH responses was effected (RT1.B 47%, p=0.001, and RT1.D 67%, p<0.001). In addition, oral administration of either allopeptide mixture resulted in significant reduction of DTH responses to allogeneic WF splenocytes (RT1.B 42% and RT1.D 48%, p<0.05, n=5 in each group, data not shown). These data indicate that oral administration of polymorphic Class II MHC allopeptides down-regulates the systemic cell mediated response to subsequent immunization, and that this down-regulation is specific to the orally administered antigens. In vitro, cervical lymph node cells harvested 3 days after the last feeding from naive animals which received the oral allopeptide mixture exhibited a marked reduction of MLR proliferation to WF stimulator cells as compared to naive controls (73% reduction, n=3, p<0.001, data not shown).

EXAMPLE 4

Figure 5A:
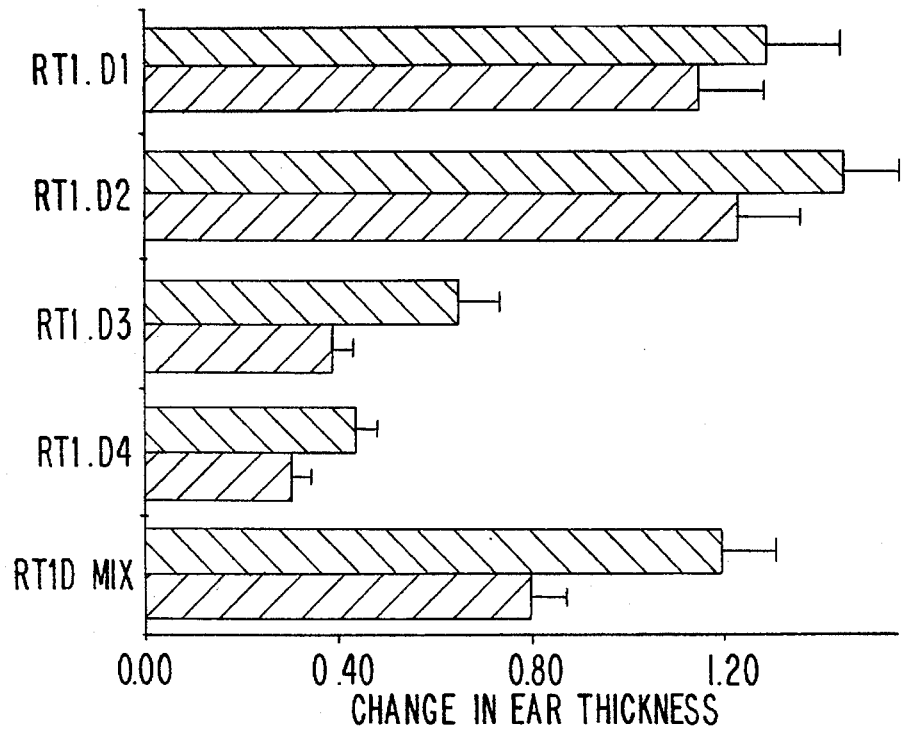
FIG. 5 is a bar graph of DTH responses of animals immunized with the individual four fragments of RT1.B (B) and RT1.D (A) and challenged with the respective allopeptide.
Figure 5B:
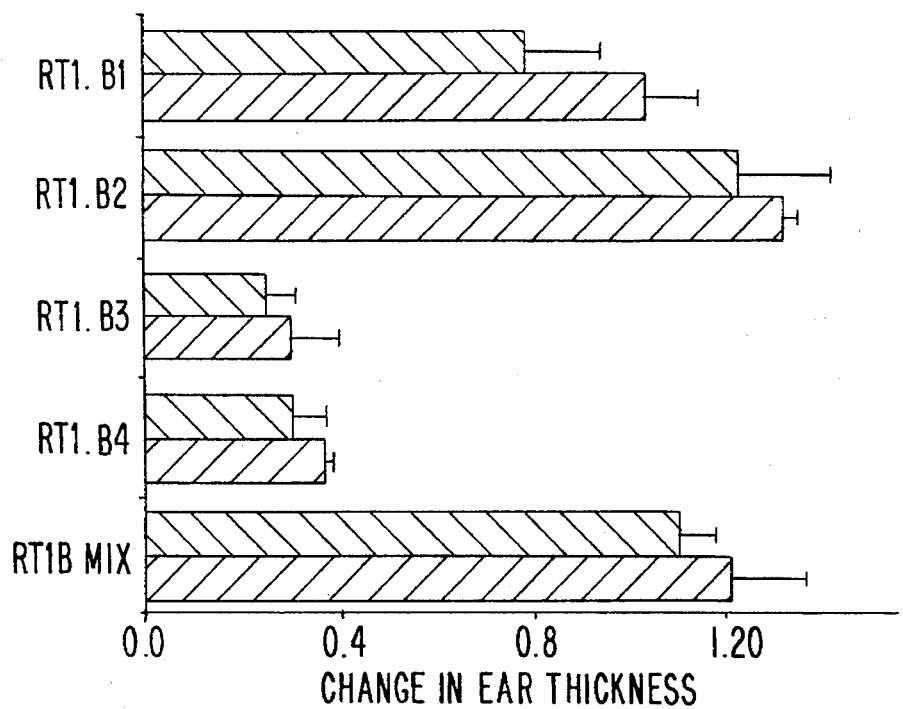

Specificity of Immunogenicity and Tolerogenicity of Class II MHC Allopeptides These experiments investigate whether, in addition to polymorphism, the native location of the allopeptide, β-pleat vs. α-helix, may be an important determinant of immunogenicity and tolerogenicity in vivo. The immunogenicity and tolerogenicity of the individual allopeptide fragments were investigated. LEW rats, used as responders, were immunized subcutaneously in the foot pad with 12.5 μg of one of the four RT1.D (1–25, 20–44, 39–64, and 60–84) and four RT1.B (1–25, 20–44, 39–64, and 68–92) allopeptide fragments and CFA. DTH responses were then determined for each of the peptide fragments. As seen in FIG. 5, only the first (RT1.B1 and RT1.D1, both 1–25) and second (RT1.B2 and RT1.D2, both 20–44) fragments corresponding to the β-pleat of both RT1.B and RT1.D, were immunogenic. In FIG. 5, "RT1D mix" and "RT1B mix" refers to animals immunized with a mixture of all four allopeptides. In FIG. 5 solid bars represent immunization with cells, hatched bars represent immunization with peptides. Bars represent the change in ear thickness in inches×$10^2$ (mean±SEM).

Oral administration of 25 μg of the combined immunogenic allopeptide fragments RT1.D1 plus RT1.D2 (12.5 μg each) but not RT1.D3 (39–64) plus RT1.D4 (60–84) resulted in significant reduction of DTH response to the RT1.D allopeptide mixture (75% reduction (P=0.005) vs. 14% reduction (P not significant); n=5 in each group). These observations, in addition to showing that the native location of the allopeptide (β-pleat vs. α-helix) is an important determinant of immunogenicity and tolerogenicity, also provide negative peptide controls for the observed specificity of immunogenicity and tolerogenicity.

EXAMPLE 5

In the following experiment, induction of antigen-specific tolerance to allografts is achieved by injection of polymorphic Class II MHC oligopeptides according to the invention.

A mixture of equal amounts (by weight) of the 8 synthetic 25-mer peptides from Example 4 representing full sequences of both RT1.Bβ$^u$ and RT1.Dβ$^u$ (FIG. 6) at a collective concentration of 1 mg/ml in phosphate buffer saline (PBS) was prepared.

Aliquots of this preparation (50 μl in each thymol lobe) were injected intrathymically in adult male LEW rats 48 hours before these rats receive WF or "third-party" BN renal allografts. Negative controls received PBS alone. BN-grafted animals that received intrathymic RT1.Bβ$^μ$ and RT1.Dβ$^μ$, animals that received intrathymic RT1.Dα (100 μg (50 μg each thymol lobe)), animals that received intrathymic RT1.Bβ$^μ$ or RT1.Dβ$^μ$ (100 μg (50 μg each thymol lobe)), animals that received intravenous RT1.Bβ$^μ$ and RT1.Dβ$^μ$, and animals that received intrathymic RT1.Bβ$^μ$ and RT1.Bβ$^μ$ (100 μg (50μ each thymol lobe)) followed by thymectomy on the day of the transplant were the positive controls. No animals received immunosuppression or antibodies. The results were as follows:

| Group | Survival (days) |
|---|---|
| Intrathymic RT1.Bβ$^μ$ + RT1.Dβ$^μ$ WF Grafts Negative Control | 7, 8, 10, >144, 145, 149, 179, 185, 186 |
| Intrathymic PBS Positive Controls | 6, 6, 7, 7, 8, 10 |
| Intrathymic RT1.B$^μ$ + RT1.D$^μ$ BN Grafts | 6, 7, 7, 7, 8, 9 |
| Intrathymic RT1.Dα | 6, 9, 9, 10 |
| Intrathymic RT1.Bβ$^μ$ or RT1.Dβ$^μ$ | 5, 6, 7, 7, 7, 8, 8, 9 |
| Intravenous RT1.Bβ$^μ$ + RT1.Dβ$^μ$ | 8, 8, 9, 10 |
| Intrathymic RT1.Bβ$^μ$ + RT1.Dβ$^μ$ (thymectomy on day of transplant) | 8, 9, 10, 10 |

Figure 7:
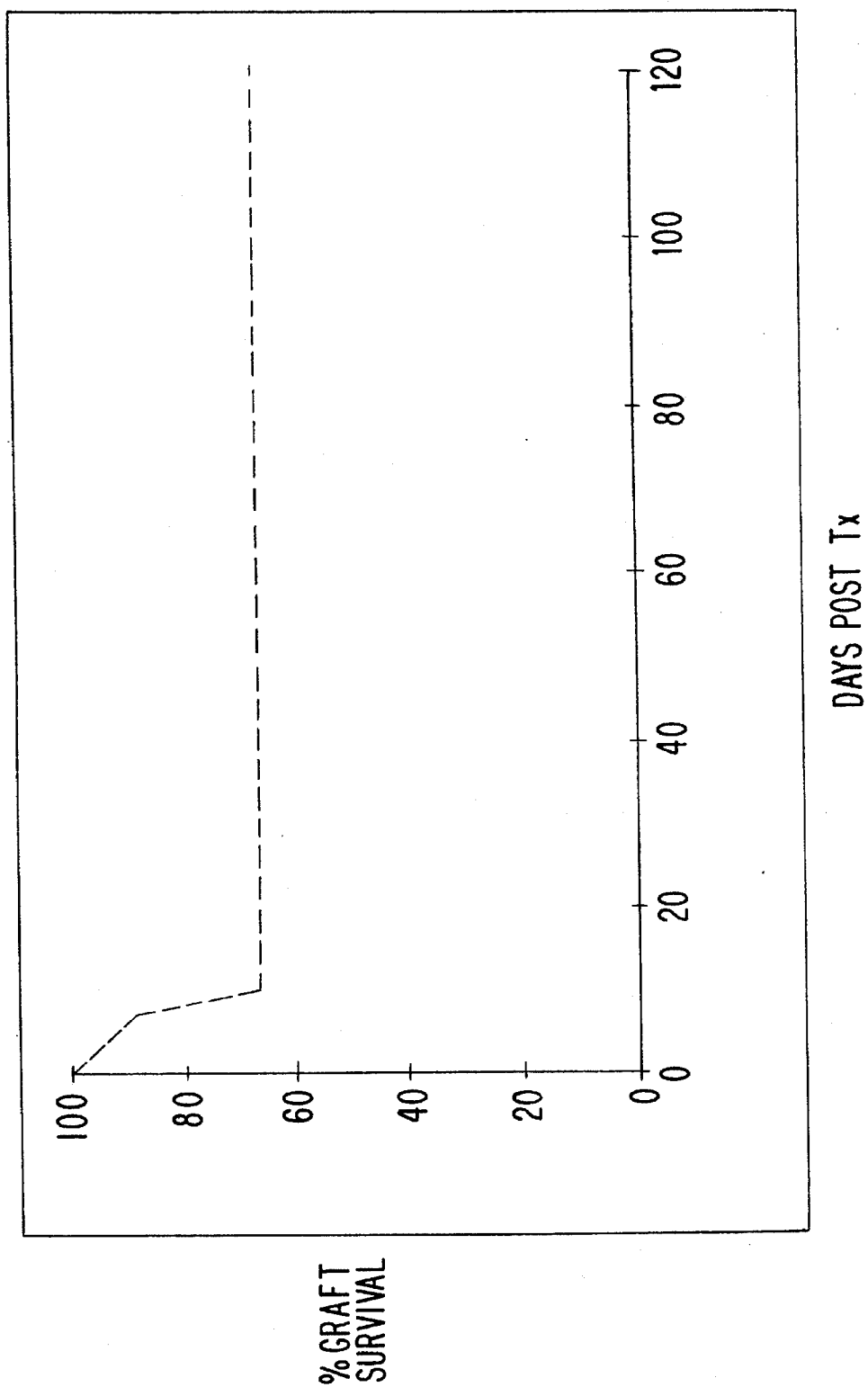
FIG. 7: A graphic illustration of graft survival rate after receipt of allografts.
Figure 8:
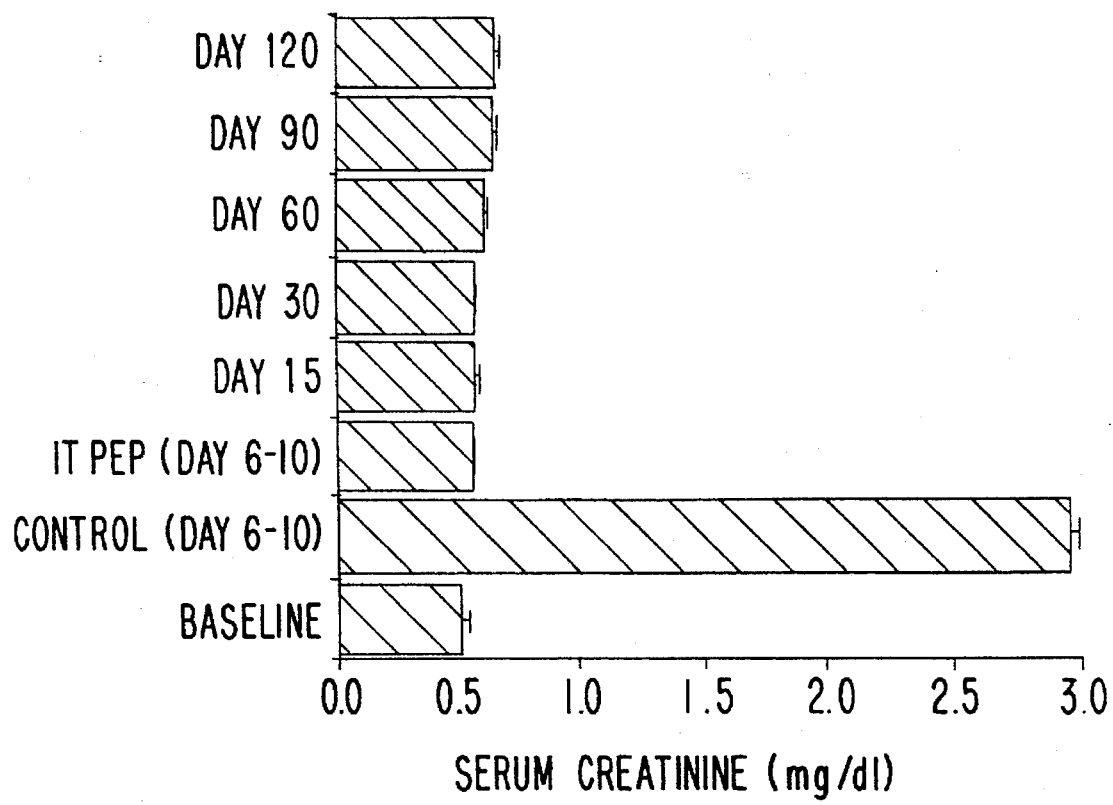
FIG. 8: A graphic illustration of allograft functions as evidenced by serum creatinine.

Negative and "third-party" (BN grafts) control animals rejected their grafts within 6–10 days as evidenced by serum creatinine levels of 2.8–3.2 mg/dl (FIG. 8). By contrast, 6 out of 9 (67%) animals injected intrathymically with Class II MHC peptides displayed significant tolerance, have not rejected their kidneys and have survived with normal allograft function (FIG. 7). These data indicate that adult thymic T-cells recognize allo-MHC oligopeptides and promote development of antigen-specific peripheral immune tolerance. Polymorphic β chains of Class II MHC allopeptides alone were sufficient to down-regulate the immune response to vascularized renal allografts, confirming and emphasizing the critical role of T-cell recognition of Class II MHC antigens in mediating allotolerance. However, intrathymic injection of RT1.Bβ$^μ$ or RT1.Dβ$^μ$ alone was insufficient to prolong allograft survival. Furthermore, the alpha chain of Class II MHC, which is presumed to be non-polymorphic and is non-immunogenic in an in vivo delayed type hypersensitivity response model, did not prolong survival. These data indicate the specificity of thymic recognition of polymorphic Class II allo MHC sequences in induction of systemic tolerance to vascularized grafts.

The rejection of allografts within 8–10 days by those animals that received the allopeptide mixture intravenously or those animals that underwent thymectomy on the day of renal transplantation suggests (however, applicants do not intend to be bound by the theory) that intrathymic injection of polymorphic Class II MHC allopeptides induces a regulatory cell which down regulates the peripheral alloimmune response or anergizes peripheral T-cell clones.

It is believed that the effects seen herein could be enhanced by administration of immunosuppressive agents such as anti-lymphocytic serum or cyclosporin.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( v i ) ORIGINAL SOURCE:
( A ) ORGANISM: Rattus rattus
( B ) STRAIN: WF ( v i i ) IMMEDIATE SOURCE:
( B ) CLONE: RTI.Bb 1-25

( x i ) SEQUENCE DESCRIPTION: SEQ ID NO:1:

```
Gln Arg Leu Arg Arg Asp Phe Leu Val Gln Phe Lys Pro Tyr Cys Tyr
1               5                   10                  15
Phe Thr Asn Gly Thr Gln Arg Ile Arg
                20                  25
```

( 2 ) INFORMATION FOR SEQ ID NO:2:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( v i ) ORIGINAL SOURCE:
    ( A ) ORGANISM: RATTUS RATTUS
    ( B ) STRAIN: WF ( v i i ) IMMEDIATE SOURCE:
    ( B ) CLONE: RT1.Bb 20-44

( x i ) SEQUENCE DESCRIPTION: SEQ ID NO:2:

```
Gly Thr Gln Arg Ile Arg Asn Val Ile Arg Tyr Ile Tyr Asn Arg Glu
 1               5                  10                      15
Glu Tyr Leu Arg Tyr Asp Ser Asp Val
                20              25
```

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: RATTUS RATTUS
        ( B ) STRAIN: WF ( v i i ) IMMEDIATE SOURCE:
        ( B ) CLONE: RT1.Bb 39-64

( x i ) SEQUENCE DESCRIPTION: SEQ ID NO:3:

```
Arg Tyr Asp Ser Asp Val Gly Glu Tyr Arg Ala Val Thr Glu Leu Gly
 1               5                  10                      15
Arg Pro Ser Ala Glu Tyr Phe Asn Lys Gln
                20              25
```

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: RATTUS RATTUS
        ( B ) STRAIN: WF ( v i i ) IMMEDIATE SOURCE:
        ( B ) CLONE: RT1.Bb68-92

( x i ) SEQUENCE DESCRIPTION: SEQ ID NO:4:

```
Leu Glu Arg Thr Arg Ala Glu Leu Asp Thr Val Cys Arg His Asn Tyr
 1               5                  10                      15
Glu Lys Thr Glu Val Pro Thr Ser Leu
                20              25
```

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: RATTUS RATTUS (B) STRAIN: WF (vii) IMMEDIATE SOURCE:
(B) CLONE: RT1.Db 1-25

(xi) SEQUENCE DESCRIPTION: SEQ ID NO:5:

Arg Asp Pro Thr Pro Arg Phe Leu Gly Tyr Leu Lys Pro Glu Cys His
1               5                   10                  15
Phe Tyr Asn Gly Thr Asn Arg Val Arg
            20              25

(2) INFORMATION FOR SEQ ID NO:6:

(i) SEQUENCE CHARACTERISTICS:
(A) LENGTH: 25 amino acids
(B) TYPE: amino acid
(D) TOPOLOGY: linear (ii) MOLECULE TYPE: peptide (vi) ORIGINAL SOURCE:
(A) ORGANISM: RATTUS RATTUS
(B) STRAIN: WF (vii) IMMEDIATE SOURCE:
(B) CLONE: RT1.Db 20-44

(xi) SEQUENCE DESCRIPTION: SEQ ID NO:6:

Gly Thr Asn Arg Val Arg Leu Leu Ala Arg Leu Ile Tyr Asn Arg Glu
1               5                   10                  15
Glu Tyr Ala Arg Phe Asp Ser Asp Val
            20              25

(2) INFORMATION FOR SEQ ID NO:7:

(i) SEQUENCE CHARACTERISTICS:
(A) LENGTH: 26 amino acids
(B) TYPE: amino acid
(D) TOPOLOGY: linear (ii) MOLECULE TYPE: peptide (vi) ORIGINAL SOURCE:
(A) ORGANISM: RATTUS RATTUS
(B) STRAIN: WF (vii) IMMEDIATE SOURCE:
(B) CLONE: RT1.Db 39-64

(xi) SEQUENCE DESCRIPTION: SEQ ID NO:7:

Arg Phe Asp Ser Asp Val Gly Glu Tyr Arg Ala Val Thr Glu Leu Gly
1               5                   10                  15
Arg Pro Ser Ala Glu Tyr Arg Asn Lys Gln
            20              25

(2) INFORMATION FOR SEQ ID NO:8:

(i) SEQUENCE CHARACTERISTICS:
(A) LENGTH: 25 amino acids
(B) TYPE: amino acid
(D) TOPOLOGY: linear (ii) MOLECULE TYPE: peptide (vi) ORIGINAL SOURCE:
(A) ORGANISM: RATTUS RATTUS
(B) STRAIN: WF (vii) IMMEDIATE SOURCE:
(B) CLONE: RT1.Db 60-84

(x i) SEQUENCE DESCRIPTION: SEQ ID NO:8:

Tyr Arg Asn Lys Gln Lys Glu Pro Met Glu Arg Arg Arg Ala Thr Val
1               5                   10                  15
Asp Thr Tyr Cys Arg His Asn Tyr Glu
            20                  25

What is claimed is:

1. A method for suppressing the ability of T-cells from a first mammal to proliferate in response to stimulation by nonself mammalian tissue comprising orally administering to said mammal a composition comprising at least one member selected from the group consisting of: (i) a major histocompatibility complex Class II antigen from a second nonself mammal or from tissue of a mammal syngeneic to said nonself mammal; (ii) at least one synthetic peptide corresponding to a T-cell suppressive fragment of said Class II antigen, said composition being administered in an amount effective to suppress said proliferation.

2. The method of claim 1 wherein said peptide is selected from the group consisting of peptides having at least 13 aminoacids and corresponding in amino acid sequence to portions of the polymorphic region of the beta chain of the RT1 domain of mouse Class II major histocompatibility complex, and both of said first mammal and said second nonself mammal are rats.

3. A method for suppressing immune response which leads to allograft rejection in a mammal receiving an allograft from a donor mammal comprising: prior to said rejection orally or enterally administering to said allograft-receiving mammal a composition comprising at least one member selected from the group consisting of (i) a Class II major histocompatibility complex antigen from the donor mammal or from a mammal syngeneic to the donor mammal; (ii) a synthetic peptide corresponding to an immune response suppressive fragment of said Class II antigen said composition being administered in an amount effective to suppress said response.

* * * * *